US006954516B2

(12) United States Patent
Li et al.

(10) Patent No.: US 6,954,516 B2
(45) Date of Patent: Oct. 11, 2005

(54) IMAGING SYSTEMS AND METHODS

(75) Inventors: Jianying Li, New Berlin, WI (US); John Michael Sabol, Sussex, WI (US); Thomas L. Toth, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 146 days.

(21) Appl. No.: 10/389,117

(22) Filed: Mar. 14, 2003

(65) Prior Publication Data

US 2004/0179646 A1 Sep. 16, 2004

(51) Int. Cl.[7] .................................. G21K 3/00
(52) U.S. Cl. .................. 378/157; 378/159; 378/16
(58) Field of Search .................. 378/156–159, 378/16

(56) References Cited

U.S. PATENT DOCUMENTS

| | | | | | |
|---|---|---|---|---|---|
| 3,819,937 | A | * | 6/1974 | Sovijarvi et al. | 378/158 |
| 5,107,529 | A | * | 4/1992 | Boone | 378/157 |
| 5,287,396 | A | * | 2/1994 | Stegehuis | 378/98.2 |
| 5,677,943 | A | * | 10/1997 | Hoebel | 378/156 |
| 5,706,326 | A | | 1/1998 | Gard | |
| 6,307,918 | B1 | | 10/2001 | Toth et al. | |
| 6,633,627 | B2 | * | 10/2003 | Horiuchi | 378/156 |

* cited by examiner

*Primary Examiner*—Craig E. Church
*Assistant Examiner*—Thomas R. Artman
(74) *Attorney, Agent, or Firm*—Carl B. Horton, Esq.; Armstrong Teasdale LLP

(57) ABSTRACT

A method for obtaining data includes scanning an organ with an imaging system emitting X-rays and modulating the emitted X-rays with an organ specific bowtie addition.

25 Claims, 4 Drawing Sheets

Original 200mA scan

Original 320mA scan

Simulated 210mA scan

IMAGING SYSTEMS AND METHODS

BACKGROUND OF THE INVENTION

This invention relates generally to medical imaging and, more particularly, to medical imaging using bowtie filters.

At least some known bowties used in current Computed Tomographic (CT) scanners are designed for general uses. For example, a General Electric LightSpeed scanner commercially available from General Electric Medical Systems of Waukesha Wis. has a head bowtie for the head and pediatric applications and a body bowtie for adult body scans. The body bowtie was designed to provide a fairly uniform X-ray flux on the detector surface after the X-rays pass through the body, therefore providing relatively equivalent image quality (noise) for the whole imaging area. This, however, may not be necessary if one is only interested in specific organs, such as a heart, and may introduce extra surface dose to the patient that may not improve the image quality of the specific organs that one is interested in.

BRIEF DESCRIPTION OF THE INVENTION

In one aspect, a method for obtaining data includes scanning an organ with an imaging system emitting X-rays and modulating the emitted X-rays with an organ specific bowtie addition.

In another aspect, a method for scanning an object with an imaging system having a bowtie filter is provided. The method includes positioning a bowtie addition in the imaging system, and scanning an object.

In yet another aspect, a collimator assembly for an imaging system is provided. The collimator assembly includes a bowtie filter, and a bowtie addition positioned proximate the bowtie filter.

In still another aspect, an imaging system is provided. The imaging system includes a radiation source, a radiation detector positioned to receive X-rays from the source, a bowtie filter positioned between the radiation source and the radiation detector, a bowtie addition positioned between the radiation source and the radiation detector, and a computer operationally coupled to the radiation source and the radiation detector, the computer is configured to scan objects.

In another aspect, a Computed Tomography (CT) imaging system includes a radiation source, a radiation detector positioned to receive X-rays from the source, a bowtie filter positioned between the radiation source and the radiation detector, a bowtie addition positioned between the radiation source and the radiation detector, and a computer operationally coupled to the radiation source and the radiation detector, the computer is configured to perform CT scans.

In one aspect, a Computed Tomography (CT) imaging system includes a radiation source, a radiation detector positioned to receive X-rays from the source, a bowtie filter positioned between the radiation source and the radiation detector, a bowtie addition comprising a plurality of thick sections interspersed with a plurality of thin sections positioned between the bowtie filter and the radiation detector, and a computer operationally coupled to the radiation source and the radiation detector, the computer is configured to perform CT scans of hearts.

DETAILED DESCRIPTION OF THE INVENTION

Figure 1:
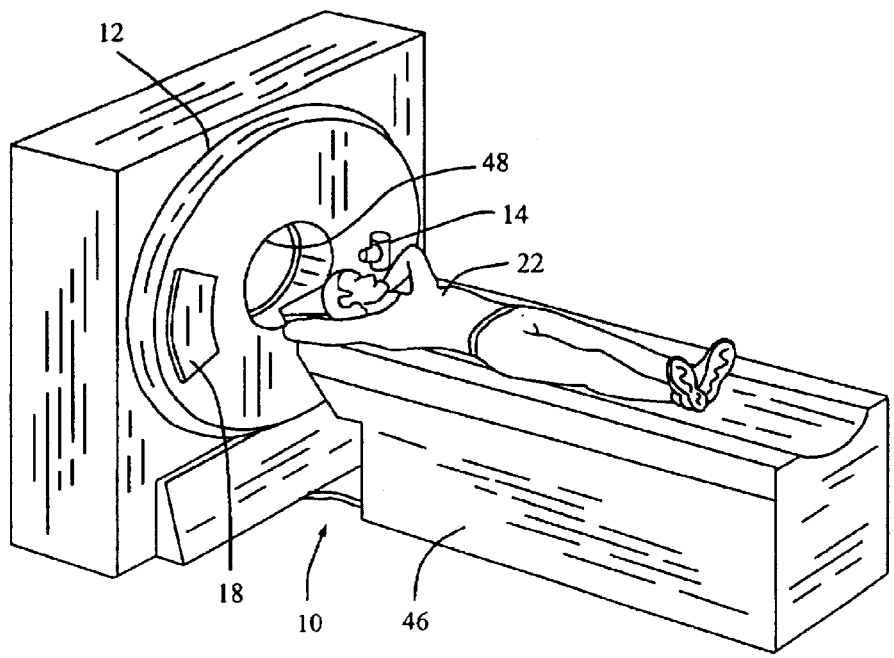
FIG. 1 is a pictorial view of a CT imaging system.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
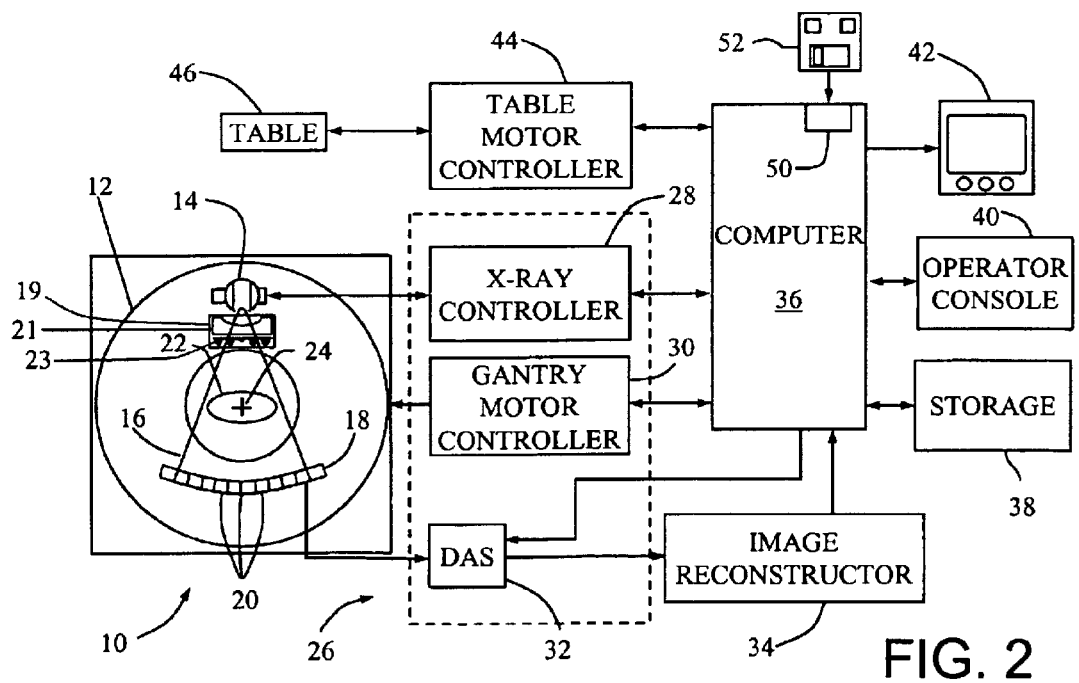
FIG. 2 is a block schematic diagram of the system illustrated in FIG. 2.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. A collimator assembly 19 is positioned between array 18 and source 14. Collimator assembly 19 includes a known bowtie filter 21 and a bowtie addition 23. Bowtie addition 23 is fabricated from any material suitable for fabricating known bowtie filters. In one embodiment, bowtie addition 23 is positioned between bowtie filter 21 and array 18. Alternatively, addition 23 is positioned between bowtie filter 21 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector-rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center, and that addition 23 is used for objects other than organs.

Herein are described novel methods and apparatus for use in imaging systems. In one aspect, the use of an organ-specific bowtie addition (e.g., bowtie addition 23) together with bowtie 21 for imaging specific organs results in the use of less dose but equal noise as with the use of bowtie 21 singularly. A set of organ-specific bowtie additions are made to modulate the X-ray flux coming out of the tube-bowtie assembly (e.g., collimator assembly 19) based on the specific organs that a physician is interested in. In one embodiment, the addition has a smooth surface and can be moved in and out of collimator assembly 19 easily by an operator. In an exemplary embodiment, bowtie addition 23 is mounted within collimator assembly 19 such that the operator can remove bowtie addition 23 without tools. Additionally, the operator can replace bowtie addition 23 with another bowtie addition without the use of tools. The additions maintain a majority of the x-ray flux coming out of bowtie 21 for the interested organ area while reducing X-ray flux for other areas, therefore reducing the whole body dose. Special bowtie additions may be made for, but certainly not limited to, the CT applications of cardiac, lung, and liver.

Figure 3:
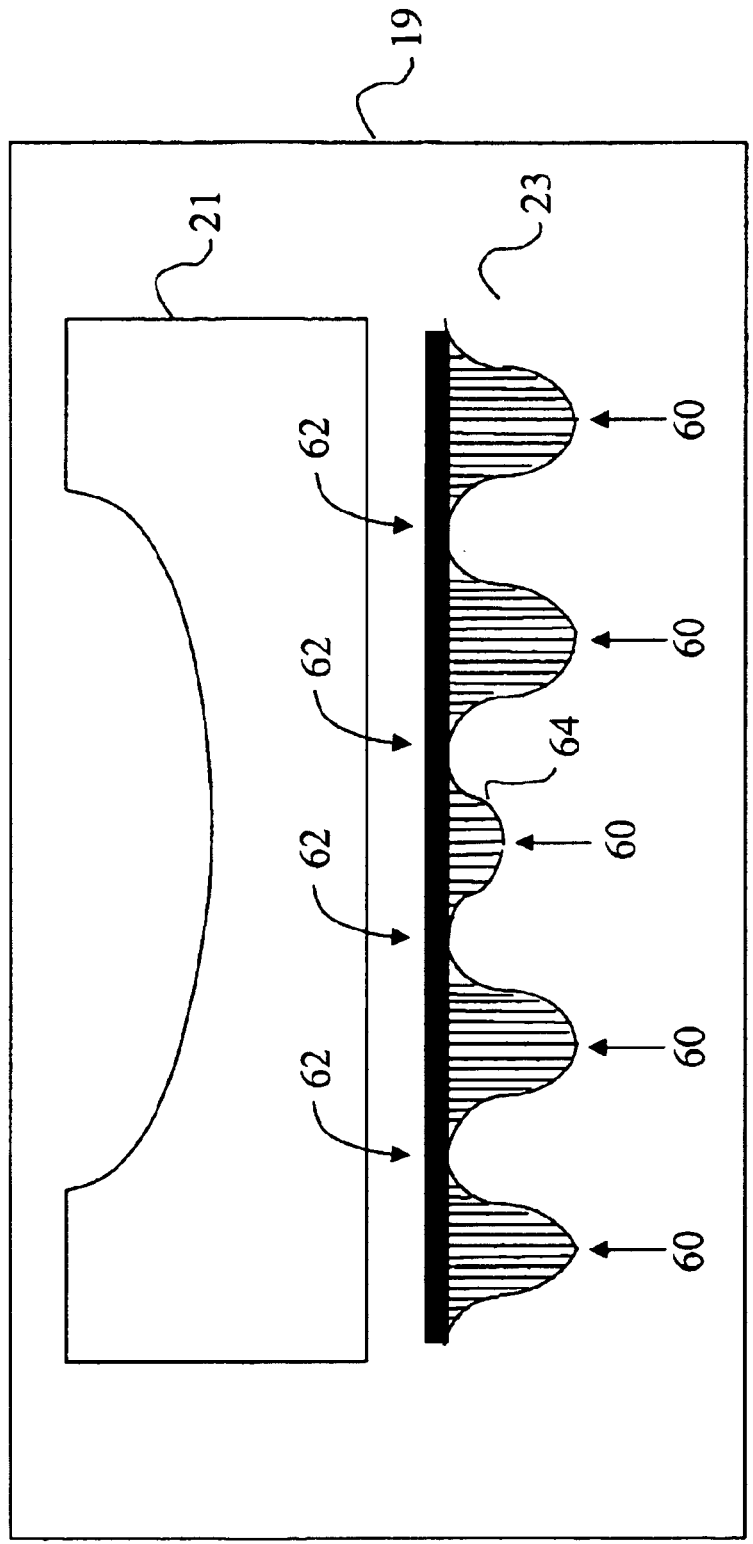
FIG. 3 is a more detailed view of the collimator assembly shown in FIG. 2.
Figure 4:
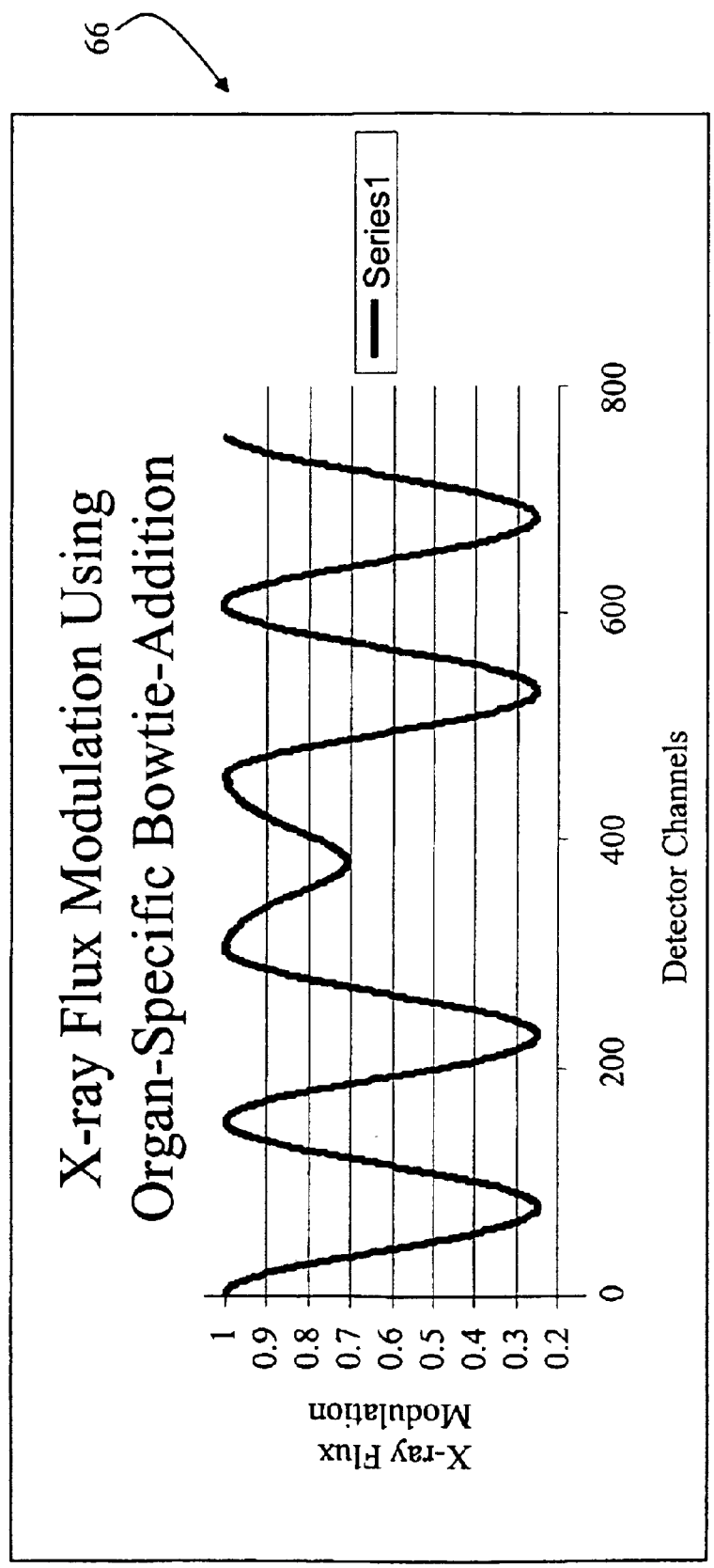
FIG. 4 illustrates an X-ray modulation 24 corresponding to the bowtie addition shown in FIGS. 2 and 3.

As illustrated in FIG. 3, bowtie addition 23 is a specific example of a bowtie addition for cardiac imaging. Bowtie addition 23 has a smooth surface and is able to move in and out of collimator assembly 19 easily. For cardiac imaging, one can use a known head bowtie or a modified head bowtie that provides more attenuation of the X-ray towards the edge of the body than the current head bowtie. This modified head bowtie provides more X-ray flux than the current body bowtie near the center of the imaging field of view where the heart is located, while reducing the dose to the whole body by at least 20%. This modified head bowtie can also be used for the general head and pediatric scans. Combined with this modified head bowtie, a bowtie addition for cardiac imaging is also used such as bowtie addition 23. Cardiac bowtie addition 23 is designed to account for the fact that the heart is not located exactly at the center of the imaging field of view, and that X-ray flux requirement for the lung area is substantially less. In the exemplary example of a cardiac bowtie addition as shown in FIG. 3 includes a plurality of thick sections 60 interspersed with a plurality of thin sections 62. A middle thick section 64 is less thick than the other thick sections 60. Although thick section 64 can be between one-third and two-thirds the thickness of other thick sections 60, thick section 64 is always about one-half the thickness of the other thick sections 60. In another example, bowtie addition 23 has more than 5 sections. In yet another example, bowtie addition 23 has 9 sections. In still another embodiment, bowtie addition 23 has 12 sections. In a further embodiment, bowtie addition 23 has at least one but less than 5 sections. In an additional embodiment, bowtie addition 23 has 4 sections. An X-ray modulation 66 is shown in FIG. 4. X-ray modulation 66 corresponds to bowtie addition 23 having 5 sections.

Figure 5:
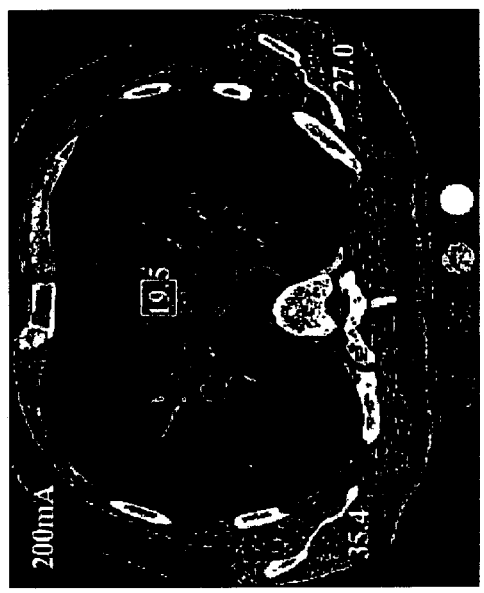
FIG. 5 illustrates an image comparison from three different sets of data.
Figure 5:
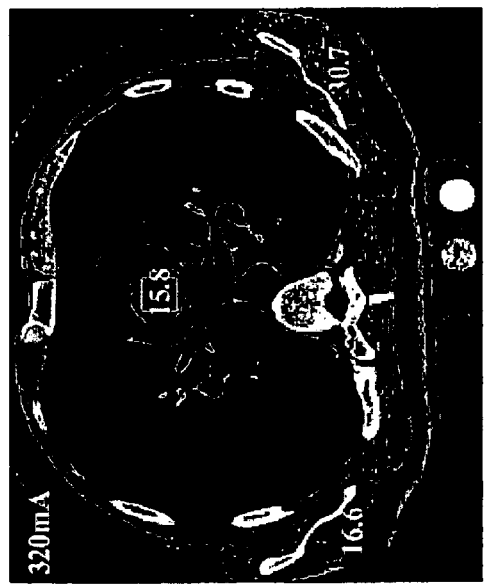
Figure 5:
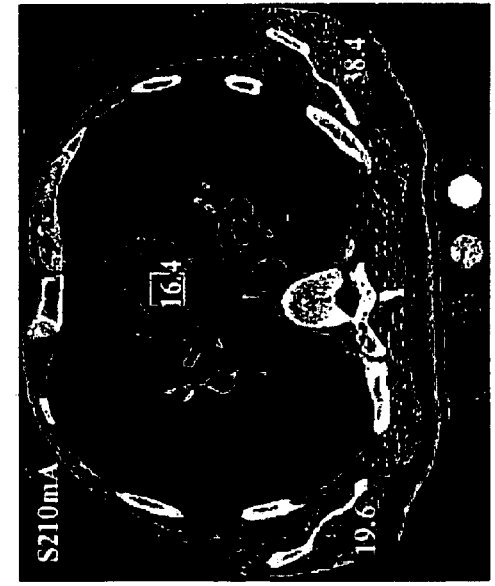

Cardiac bowtie addition 23 has been evaluated using patient scans. Two sets of cardiac scans were obtained at both 320 mA and 200 mA for clinical evaluation. Lower dose scans (210 mA average) with the X-ray modulated according to the cardiac bowtie addition was simulated using a noise addition tool based on the original 320 mA scans. These three sets of scan data were reconstructed using the standard reconstruction algorithm. Image noises were measured at three different locations on three sets of images. FIG. 5 shows the image comparison from the three different sets of data. Also shown on the images are the noise measurements. The comparison indicates that (1) using the current body bowtie for cardiac imaging, the noise increases as the mA decreases. The discrepancies of the edge noise numbers were caused by the current fan beam reconstruction algorithm. After the two numbers were averaged, they still follow the inverse square root of the mA rule. And (2), with the use of bowtie addition 23, the noise measurements in the heart area of the simulated lower dose scans were about the same as the original scans, even through the average mA (dose) has decreased by 30%.

Exemplary embodiments of methods, systems, and assemblies for facilitating a reduction in patient dose are described above in detail. The methods, systems, and assemblies are not limited to the specific embodiments described herein, but rather, components of each methods, systems, and assemblies may be utilized independently and separately from other components described herein. In addition, each methods, systems, and assemblies component can also be used in combination with other components described herein.

While the invention has been described in terms of various specific embodiments, those skilled in the art will recognize that the invention can be practiced with modification within the spirit and scope of the claims.

What is claimed is:

1. A method for obtaining data, said method comprising:
    scanning an organ with an imaging system emitting X-rays; filtering the emitted x-rays with a bowtie filter; and
    modulating the emitted X-rays with an organ specific bowtie addition, wherein the bowtie addition comprises a plurality of thick sections interspersed with a plurality of thin sections.

2. A method for scanning an object with an imaging system having a bowtie filter, said method comprising:
    positioning a bowtie addition in the imaging system, wherein the bowtie addition comprises a plurality of thick sections interspersed with a plurality of thin sections; and
    scanning an object.

3. A method in accordance with claim 2 wherein said positioning a bowtie addition comprises positioning a first organ specific bowtie addition in the imaging system, said scanning comprises scanning a first organ, said method further comprising:
    positioning a second organ specific bowtie addition in the imaging system different than the first organ specific bowtie addition; and
    scanning a second organ different than the first organ.

4. A method in accordance with claim 3 wherein said scanning a second organ different than the first organ comprises scanning a heart.

5. A method in accordance with claim 4 wherein said scanning a first organ comprises scanning a first organ comprising one of a lung and a liver.

6. A method in accordance with claim 2 said positioning comprises positioning a bowtie addition comprises a plurality of thick sections interspersed with a plurality of thin sections, wherein a center thick section is less thick than all other thick sections.

7. A method in accordance with claim 6 wherein said positioning comprises positioning a bowtie addition comprising five thick sections interspersed with four thin sections.

8. A method in accordance with claim 7 further wherein said positioning comprises positioning a bowtie addition comprising a middle thick section less than one-half as thick as the other thick sections.

9. A method in accordance with claim 8 wherein said scanning an object comprises scanning a heart.

10. A method in accordance with claim 2 wherein said positioning comprises positioning a bowtie addition comprising five thick sections interspersed with four thin sections.

11. A collimator assembly for an imaging system, said collimator assembly comprising:
    a bowtie filter; and
    a bowtie addition positioned proximate said bowtie filter, said bowtie addition comprises a plurality of thick sections interspersed with a plurality of thin sections.

12. A collimator assembly in accordance with claim 11 wherein said bowtie addition comprises five thick sections interspersed with four thin sections.

13. A collimator assembly in accordance with claim 12 wherein said bowtie addition comprises one thick section about one-half as thick as said other thick sections.

14. A collimator assembly in accordance with claim 13 wherein said bowtie addition comprises a middle, said thick section about one-half thick positioned in said middle.

15. An imaging system comprising:
    a radiation source;
    a radiation detector positioned to receive X-rays from said source;
    a bowtie filter positioned between said radiation source and said radiation detector;
    a bowtie addition positioned between said radiation source and said radiation detector, said bowtie addition comprises a plurality of thick sections interspersed with a plurality of thin sections; and a computer operationally coupled to said radiation source and said radiation detector, said computer configured to scan objects.

16. An imaging system in accordance with claim 15 wherein said bowtie addition comprises five thick sections interspersed with four thin sections.

17. An imaging system in accordance with claim 16 wherein said bowtie addition comprises one thick section about one-half as thick as said other thick sections.

18. An imaging system in accordance with claim 17 wherein said bowtie addition comprises a middle, said thick section about one-half thick positioned in said middle.

19. A Computed Tomography (CT) imaging system comprising:
   a radiation source;
   a radiation detector positioned to receive X-rays from said source;
   a bowtie filter positioned between said radiation source and said radiation detector;
   a bowtie addition positioned between said radiation source and said radiation detector, said bowtie addition comprises a plurality of thick sections interspersed with a plurality of thin sections; and
   a computer operationally coupled to said radiation source and said radiation detector, said computer configured to perform CT scans.

20. A CT system in accordance with claim 19 wherein said bowtie addition comprises five thick sections interspersed with four thin sections.

21. A CT system in accordance with claim 20 wherein said bowtie addition comprises one thick section about one-half as thick as said other thick sections.

22. An imaging system comprising:
   a radiation source;
   a radiation detector positioned to receive X-rays from said source;
   a bowtie filter positioned between said radiation source and said radiation detector;
   a bowtie addition comprising a plurality of thick sections interspersed with a plurality of thin sections positioned between said bowtie filter and said radiation detector; and
   a computer operationally coupled to said radiation source and said radiation detector, said computer configured to perform CT scans of hearts.

23. A Computed Tomography (CT) imaging system for scanning an object comprising:
   a radiation source;
   a radiation detector configured to receive X-rays from said source;
   a bowtie filter positioned between said radiation source and said radiation detector; and
   a bowtie addition configured to modulate the X-rays to reduce a dose of the X-rays outside an area of interest that is located on the object, said bowtie addition is further configured to maintain the dose within the area of interest; and
   a computer operationally coupled to said radiation source and said radiation detector, said computer configured to perform CT scans.

24. A method for scanning an object with an imaging system having a bowtie filter and a bowtie addition, said method comprising:
   using a dose of an X-ray flux to perform a scan of the object; and
   using the bowtie addition to modulate the X-ray flux to reduce the dose of the X-ray flux outside an area of interest located on the object and to maintain the dose of the X-ray flux within the area of interest.

25. A method in accordance with claim 24 wherein said modulating comprises modulating the X-ray flux to reduce the dose of the X-ray flux outside an area of interest comprising at least one organ of the object.

* * * * *